(12) United States Patent
Ko

(10) Patent No.: US 10,575,894 B2
(45) Date of Patent: Mar. 3, 2020

(54) ELECTRODE FOR HIGH-FREQUENCY SURGERY, HIGH-FREQUENCY SURGERY DEVICE, AND METHOD FOR CONTROLLING SAME

(71) Applicant: Lutronic Corporation, Gyeonggi-do (KR)

(72) Inventor: Kwang Chon Ko, Gyeonggi-do (KR)

(73) Assignee: Lutronic Corporation, Goyang-si, Gyeonggi-do (KR)

( * ) Notice: Subject to any disclaimer, the term of this patent is extended or adjusted under 35 U.S.C. 154(b) by 453 days.

(21) Appl. No.: 15/410,169

(22) Filed: Jan. 19, 2017

(65) Prior Publication Data

US 2017/0128124 A1    May 11, 2017

Related U.S. Application Data

(63) Continuation-in-part of application No. 14/388,574, filed as application No. PCT/KR2012/002223 on Mar. 27, 2012, now Pat. No. 9,561,072.

(30) Foreign Application Priority Data

Mar. 27, 2012  (KR) ........................ 10-2012-0031075

(51) Int. Cl.
  *A61B 18/14*  (2006.01)
  *A61B 18/12*  (2006.01)
  *A61B 18/00*  (2006.01)

(52) U.S. Cl.
  CPC .......... *A61B 18/14* (2013.01); *A61B 18/1206* (2013.01); *A61B 2018/0022* (2013.01);
(Continued)

(58) Field of Classification Search
  CPC ............ A61B 18/14; A61B 2018/0022; A61B 2018/00267; A61B 18/1206; A61B 2018/1465
  See application file for complete search history.

(56) References Cited

U.S. PATENT DOCUMENTS 5,345,936 A   9/1994  Pomeranz et al.
6,488,673 B1 * 12/2002  Laufer .................. A61B 18/00
                                                      604/516

(Continued)

FOREIGN PATENT DOCUMENTS

JP    2004223080 A    8/2004

OTHER PUBLICATIONS

International Search Report on PCT/KR2012/002223, dated Jan. 29, 2013.

*Primary Examiner* — Jaymi E Della
*Assistant Examiner* — Rachel A. Vierra
(74) *Attorney, Agent, or Firm* — McCarter & English, LLP; David R. Burns

(57) ABSTRACT

Disclosed are an electrode for high-frequency surgery, a high-frequency surgery device, and a method for controlling same, wherein the electrode for high-frequency surgery can be easily inserted and moved inside the lumens inside the body, and can expand a conduction area of a high-frequency current after reaching an area to be treated. The electrode for the high-frequency surgery, according to the present invention, comprises: a balloon; and a conductive structure, which is arranged on the outside of the balloon and the exterior shape of which varies according to the volume of the balloon.

12 Claims, 8 Drawing Sheets

(52) U.S. Cl.
  CPC .............. *A61B 2018/00267* (2013.01); *A61B 2018/1465* (2013.01)

(56) References Cited

U.S. PATENT DOCUMENTS

| | | |
|---|---|---|
| 6,620,159 B2 | 9/2003 | Hegde |
| 7,165,551 B2 | 1/2007 | Edwards et al. |
| 7,615,049 B2 * | 11/2009 | West .................. A61B 18/1492 606/41 |
| 7,857,808 B2 | 12/2010 | Oral et al. |
| 8,021,362 B2 | 9/2011 | Deem et al. |
| 8,998,893 B2 | 4/2015 | Avitall |
| 9,131,980 B2 | 9/2015 | Bloom |
| 2005/0070888 A1 | 3/2005 | Dimatteo et al. |
| 2006/0241704 A1 | 10/2006 | Shuros et al. |
| 2007/0173939 A1 | 7/2007 | Kim et al. |
| 2008/0319350 A1 | 12/2008 | Wallace et al. |

\* cited by examiner

US 10,575,894 B2

ELECTRODE FOR HIGH-FREQUENCY SURGERY, HIGH-FREQUENCY SURGERY DEVICE, AND METHOD FOR CONTROLLING SAME

RELATED APPLICATIONS

This application is a continuation-in-part of U.S. patent application Ser. No. 14/388,574 filed Sep. 26, 2014, which is a 35 U.S.C. § 371 National Stage filing of International Application No. PCT/KR2012/002223 filed on Mar. 27, 2012, which claims the benefit of Korean Patent Application No. 10-2012-0031075 filed on Mar. 27, 2012. The entire contents of each of the foregoing applications are explicitly incorporated herein by reference.

BACKGROUND OF THE INVENTION

Field of the invention

The present invention relates to an electrode for radiofrequency surgery, a radiofrequency surgery device, and a method of controlling the same, and more particularly, to an electrode for radiofrequency surgery that is used to remove an abnormal tissue inside the body by using heat generated when a radiofrequency current is conducted, a radiofrequency surgery device, and a method of controlling the same.

Related Art

Recently, a surgery method in which an abnormal tissue inside a body is cut by using heat generated when a radiofrequency current is conducted inside the body. In the surgery method using the radiofrequency current, as compared with a surgery method in which a part of the body is cut and various surgery tools are directly inserted into the body, there are advantages in that pain is small and a treatment time and a recovery time are shortened.

The electrode for radiofrequency surgery is already disclosed in "Korean patent No. 10-0758025; electrode for radiofrequency surgery". The Patent includes a bent hollow electrode and a sharp electrode needle. Accordingly, in the Patent No. 10-0758025, a conducting part is accurately positioned, and heating of the conducting part may be precisely controlled.

However, In the Patent No. 10-0758025, since the heating of the conducting part is concentrated at a predetermined portion, there is a problem in that the radiofrequency current is not efficiently used in a wide area to be treated.

Further, in the Patent No. 10-0758025, while the bent hollow electrode is inserted or moved in the lumen of the body having a relatively narrow internal space such as esophagus, duodenum, small intestine, and large intestine, there is a problem in that the electrode needle interferes in a normal tissue to damage the normal tissue.

SUMMARY OF THE INVENTION

An aspect of the present invention provides an electrode for radiofrequency surgery that can be easily inserted and moved into a lumen of a body and expand a conduction area of a radiofrequency current after reaching an area to be treated, a radiofrequency surgery device, and a method for controlling the same.

An exemplary embodiment of the present invention provides an electrode for radiofrequency surgery including: a balloon; and a conductor which is arranged at the outside of the balloon and has an exterior shape which varies according to the volume of the balloon.

The electrode may further include first and second support rings which are spaced apart from each other with the balloon therebetween, in which the balloon may be supported by at least one of the first and second support rings.

The conductor may be a plurality of wires of which one end is coupled with the first support ring and the other end is coupled with the second support ring.

The conductor may be a plurality of coil springs of which one end is coupled with the first support ring and the other end is coupled with the second support ring.

The conductor may be a plurality of coil springs which is provided in a ring shape covering a circumference of the balloon and arranged between the first support ring and the second support ring, and the electrode may further include: a support wire connecting the first support ring and the second support ring; a first coil wire connecting some of the plurality of coil springs and the first support ring; and a second coil wire connecting the remaining coils springs which are not connected to the first support ring among the plurality of coil springs and the second support ring.

Another exemplary embodiment of the present invention provides a radiofrequency surgery device including: a balloon; a pump connected to the balloon to supply gas to the balloon; a conductor arranged on the outside of the balloon and having an exterior shape which varies according to the volume of the balloon; and a radiofrequency generator electrically connected to the conductor to generate a radiofrequency current.

The conductor may further include an opposing electrode which is inserted into the body together with the balloon to apply at least one current of a positive current and a negative current, and contact an outer skin corresponding to a position of the conductor to apply a current having an opposite polarity to the conductor.

The conductor may be divided into a plurality of conductors, a positive current may be applied to some of the plurality of conductors, and a negative current may be applied to the rest of the plurality of conductors.

The radiofrequency surgery device may further include first and second support rings which are spaced apart from each other with the balloon therebetween, in which the balloon may be supported by at least one of the first and second support rings.

The conductor may be a wire of which one end is coupled with the first support ring and the other end is coupled with the second support ring.

The conductor may be a coil spring of which one end is coupled with the first support ring and the other end is coupled with the second support ring.

The conductor may be a plurality of coil springs which is provided in a ring shape covering a circumference of the balloon and arranged between the first support ring and the second support ring, and the radiofrequency surgery device may further include: a support wire connecting the first support ring and the second support ring; a first coil wire connecting some of the plurality of coil springs and the first support ring; and a second coil wire connecting the remaining coils springs which are not connected to the first support ring among the plurality of coil springs and the second support ring.

Yet another exemplary embodiment of the present invention provides a method of controlling a radiofrequency surgery device including: an electrode inserting step in which an electrode for radiofrequency surgery is inserted into a body; an electrode expanding step in which gas is injected into the balloon provided in the electrode for radiofrequency surgery to expand the balloon, and an exterior shape of the electrode for radiofrequency surgery is expanded according to the expansion of the balloon; and a radiofrequency supplying step in which a radiofrequency current is supplied to the electrode for radiofrequency surgery.

One of a positive current and a negative current may be applied to the electrode for radiofrequency surgery, and in the frequency supplying step, the opposing electrode may contact an outer skin corresponding to a position of the electrode for radiofrequency surgery, and a current which is opposite to the electrode for radiofrequency surgery may be applied to the opposing electrode.

The electrode for radiofrequency surgery may be divided into a positive pole and a negative pole, and in the frequency supplying step, a positive current and a negative current may be supplied to the electrode for radiofrequency surgery.

According to the exemplary embodiments of the present invention, the radiofrequency current is efficiently used, the radiofrequency electrode is easily inserted and moved inside the body, and as a result, reliability of the surgery can be improved.

DESCRIPTION OF EXEMPLARY EMBODIMENTS

Hereinafter, exemplary embodiments of an electrode for radiofrequency surgery, a radiofrequency surgery device, and a method for controlling the same will be described with reference to the accompanying drawings. As those skilled in the art would realize, the described embodiments may be deformed in various different ways, all without departing from the spirit or scope of the present invention. On the contrary, exemplary embodiments introduced herein are provided to make disclosed contents thorough and complete and sufficiently transfer the spirit of the present invention to those skilled in the art.

First Exemplary Embodiment

Figure 1:
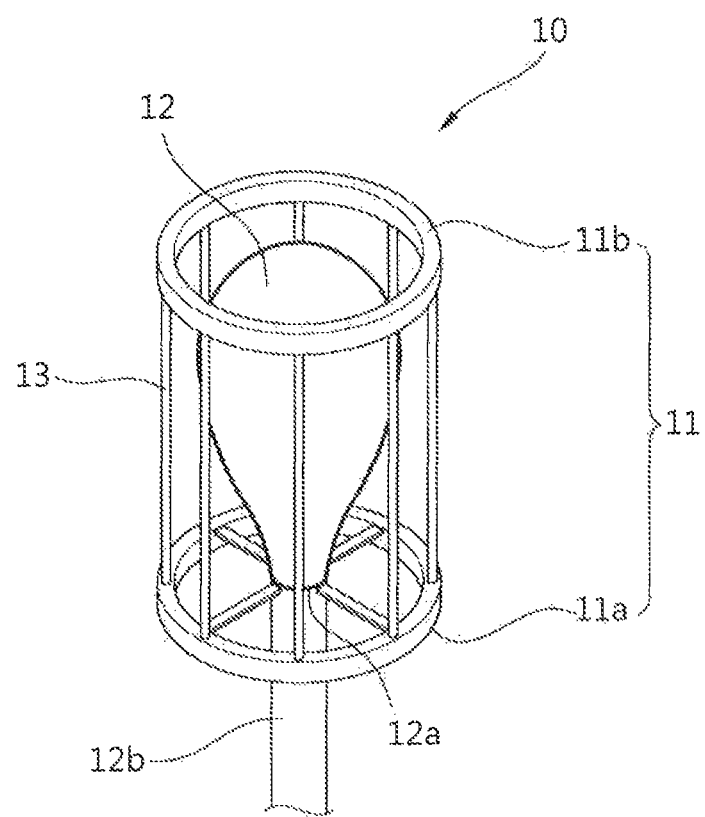
FIG. 1 is a diagram illustrating an electrode for radiofrequency surgery according to a first exemplary embodiment.

FIG. 1 is a diagram illustrating an electrode for radiofrequency surgery according to a first exemplary embodiment.

Referring to FIG. 1, an electrode 10 for radiofrequency surgery according to a first exemplary embodiment (hereinafter, referred to as an 'electrode for radiofrequency surgery') includes a supporter 11, a balloon 12, and a conductor.

The supporter 11 may be divided into a first support ring 11a and a second support ring 11b. The first support ring 11a and the second support ring 11b are spaced apart from each other with the balloon 12 therebetween. A gas inlet 12a into which gas may be injected is formed in the balloon 12. A gas supply pipe 12b may be coupled with the gas inlet 12a. The gas supply pipe 12b is coupled with the first support ring 11a. The gas inlet 12a is coupled with the gas supply pipe 12b, and as a result, the balloon 12 may be supported to the first support ring 11a. Accordingly, the balloon 12 may be moved together with the first support ring 11a.

The conductor may be provided in a form of a plurality of wires 13. In the plurality of wires 13, one end is coupled with the first support ring 11a and the other end is coupled with the second support ring 11b. The plurality of wires 13 is arranged to cover the outside of the balloon 12. Accordingly, the shape of the plurality of wires 13 may be deformed according to the volume of the balloon 12. That is, the plurality of wires 13 maintains a linear shape connecting the first support ring 11a and the second support ring 11b, and may be deformed convexly outwardly as the volume of the balloon 12 is expanded.

The plurality of wires 13 may have at least one polarity of a positive pole or a negative pole. In this case, the first support ring 11a and the second support ring 11b may be made of electro-conductive materials.

In the electrode 10 for radiofrequency surgery, the plurality of wires 13 is inserted into the body, an opposing electrode having an opposite polarity to the plurality of wires 13 contacts the outside of the body, and as a result, the plurality of wires 13 and the opposing electrode are conducted to each other to generate heat inside the body. In this case, the generated heat may remove an abnormal tissue inside the body.

Figure 2:
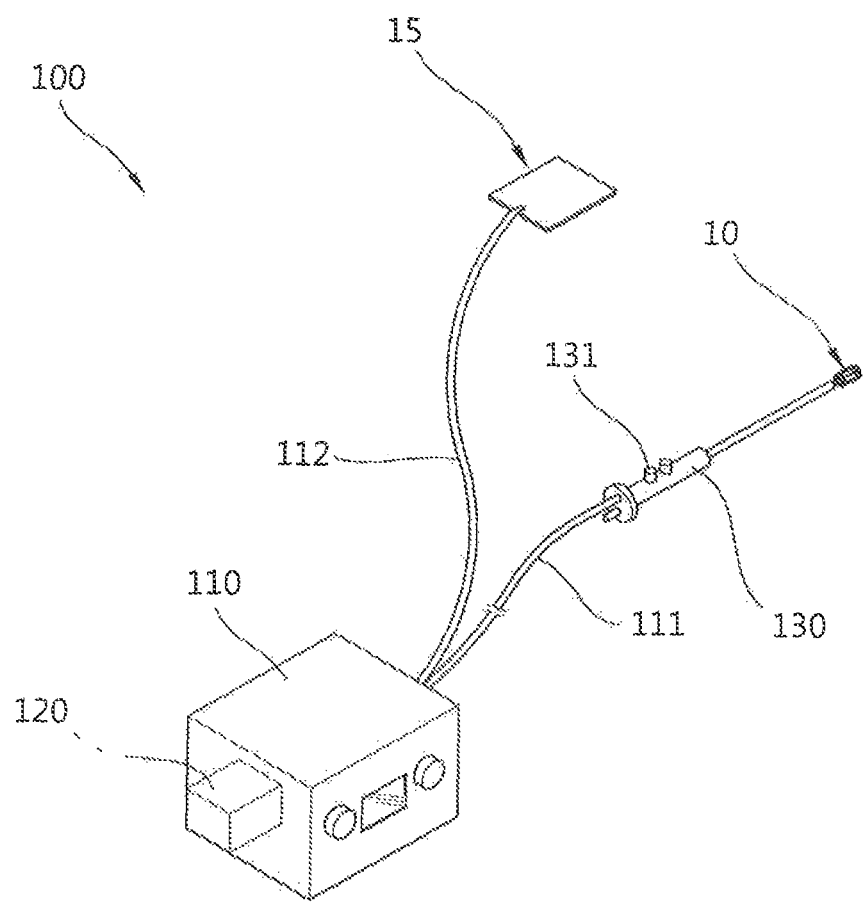
FIG. 2 is a diagram schematically illustrating a configuration of a radiofrequency surgery device according to the first exemplary embodiment.

FIG. 2 is a diagram schematically illustrating a configuration of a radiofrequency surgery device according to a first exemplary embodiment.

Referring to FIG. 2, a radiofrequency surgery device 100 according to a first exemplary embodiment (hereinafter, referred to as a 'radiofrequency surgery device') includes an electrode 10 for radiofrequency surgery, a radiofrequency generator 110, and a pump 120. The radiofrequency surgery device 100 uses the electrode 10 for radiofrequency surgery described above, and the detailed description of the electrode 10 for radiofrequency surgery may be understood with reference to the description of the electrode 10 for radiofrequency surgery described above.

The radiofrequency generator 110 generates a radiofrequency current. The radiofrequency surgery device 100 may include a first cable 111 connected to the electrode 10 for radiofrequency surgery and the radiofrequency generator 110, and a second cable 112 connected to the opposing electrode 15 and the radiofrequency generator 110. A power supply line for applying a positive or negative radiofrequency current to the electrode 10 for radiofrequency surgery is embedded in the first cable 111, and a power supply line for applying a radiofrequency current having an opposite polarity of the electrode 10 for radiofrequency surgery is embedded in the second cable 112. The power supply line embedded in the first cable 111 is electrically connected to the first support ring 11a to apply the radiofrequency current to the plurality of wires 13.

Meanwhile, the gas supply pipe 12b coupled with the balloon 12 may be embedded inside the first cable 111 together. The gas supply pipe 12b is connected to the pump 120. The pump 120 may be installed inside the radiofrequency generator 110.

Although not illustrated, an endoscope acquiring an image inside the body and an illumination ensuring illumination inside the body may be installed at a front end of the first cable 111. Further, a separate flow channel from the gas supply pipe 12b may be installed inside the first cable 111. The flow channel provides a path in which gas or a liquid may be sprayed or suctioned into the body. Further, a power supply line (not illustrated) and a signal line (not illustrated), which are connected to an endoscope (not illustrated) and an illumination (not illustrated), may be installed inside the first cable 111. Since the endoscope (not illustrated), the illumination (not illustrated), and the flow channel (not illustrated) are techniques which are widely known in the art, the detailed description thereof will be omitted.

In the above description, the endoscope (not illustrated) and the illumination (not illustrated) are installed at the front end of the first cable 111, the flow channel (not illustrated) is embedded in the first cable 111 to be operated together with the radiofrequency surgery device 100, but the endoscope (not illustrated), the illumination (not illustrated), and the flow channel (not illustrated) are provided as separate devices from the radiofrequency surgery device 100 to be operated together with the radiofrequency surgery device 100.

Meanwhile, a handpiece 130 may be installed on a line of the first cable 111. An operation button 131 is installed at the handpiece 130. The operation button 131 may smoothly control a location of the electrode 10 for radiofrequency surgery inserted into the body.

Hereinafter, a method of controlling a radiofrequency surgery device according to a first exemplary embodiment will be described.

Figure 3:
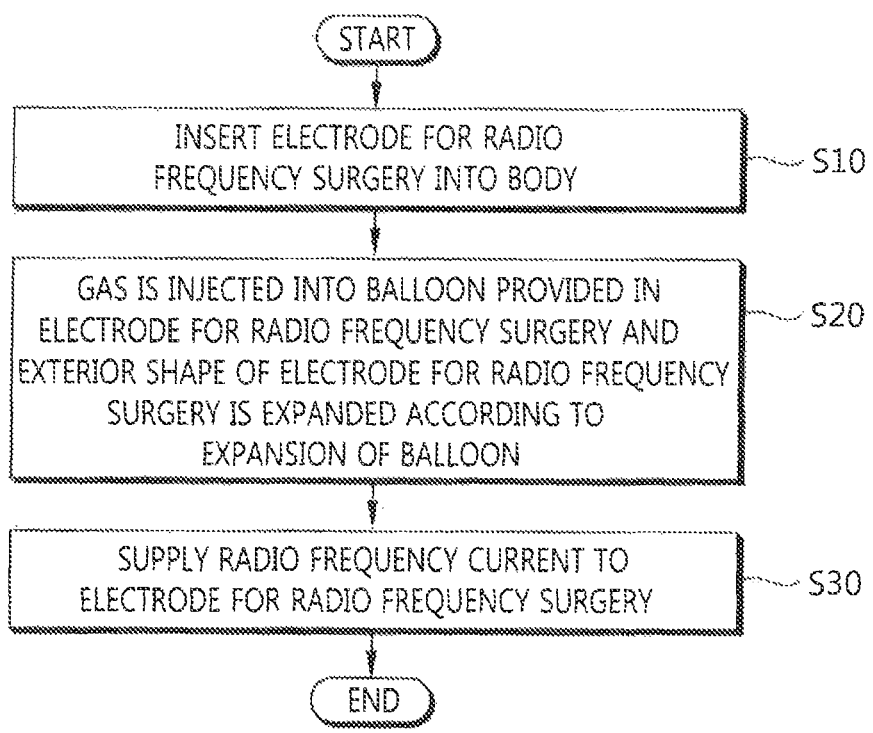
FIG. 3 is a diagram illustrating a method for controlling the radiofrequency surgery device according to the first exemplary embodiment.
Figure 4:
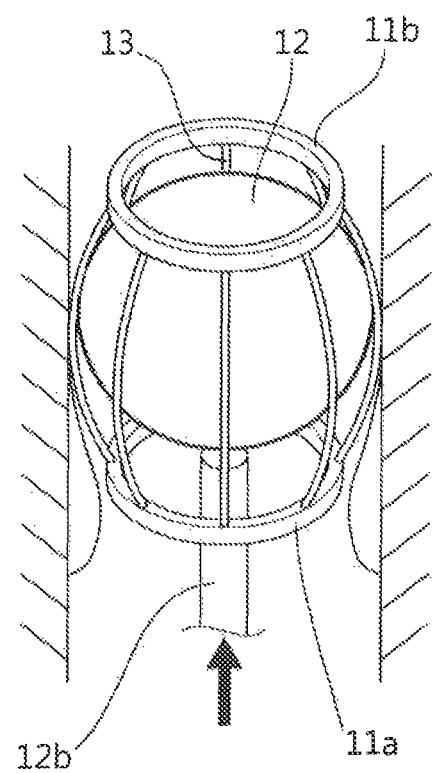
FIG. 4 is a diagram illustrating a state in which a balloon is expanded in the radiofrequency surgery device according to the first exemplary embodiment.

FIG. 3 is a diagram illustrating a method for controlling the radiofrequency surgery device according to the first exemplary embodiment, and FIG. 4 is a diagram illustrating a state in which a balloon is expanded in the radiofrequency surgery device according to the first exemplary embodiment.

Referring to FIG. 3, a user inserts the first cable 111 into a body of a patient. In this case, a catheter (not illustrated) for smoothly inserting the first cable 111 may be used. As such, when the first cable 111 is inserted into the body, the user refers to an image inside the body of the patient which is acquired by the endoscope (not illustrated) and searches the inside of the body. (Step; S10)

Next, when an abnormal tissue is detected, the user positions the electrode 10 for radiofrequency surgery around the abnormal tissue. In addition, the user contacts the opposing electrode 15 with an outer skin of the patient corresponding to the abnormal tissue.

Next, the user operates the pump 120 so that gas is supplied to the balloon 12. When the volume of the balloon 12 is expanded, the plurality of wires 13 is deformed to an outwardly convex shape. (Step; S20)

Next, the user operates the radiofrequency generator 110 so that the radiofrequency current is supplied. While the radiofrequency current is supplied, one of the positive current and the negative current applied to the plurality of wires 13 and the other current applied to the opposing electrode 15 are conducted to each other to generate heat inside the body. As such, as the radiofrequency current is conducted and the heat is generated in the body, the abnormal tissue in the body may be cut. (Step; S30)

Hereinafter, an electrode for radiofrequency surgery according to another exemplary embodiment of the present invention will be described. Hereinafter, like constituent elements described in the first exemplary embodiment described above designate like reference numerals, and the detailed description thereof will be omitted. Accordingly, hereinafter, it can be understood that the constituent elements of which the detailed description is omitted refer to the description of the first exemplary embodiment described above.

Second Exemplary Embodiment

Figure 5:
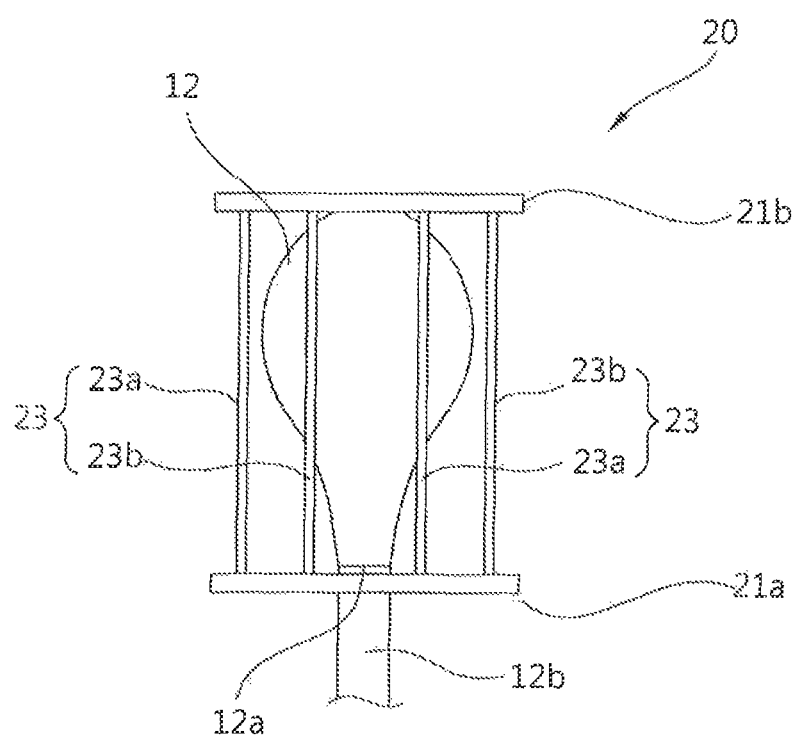
FIG. 5 is a diagram illustrating an electrode for radiofrequency surgery according to a second exemplary embodiment.
Figure 6:
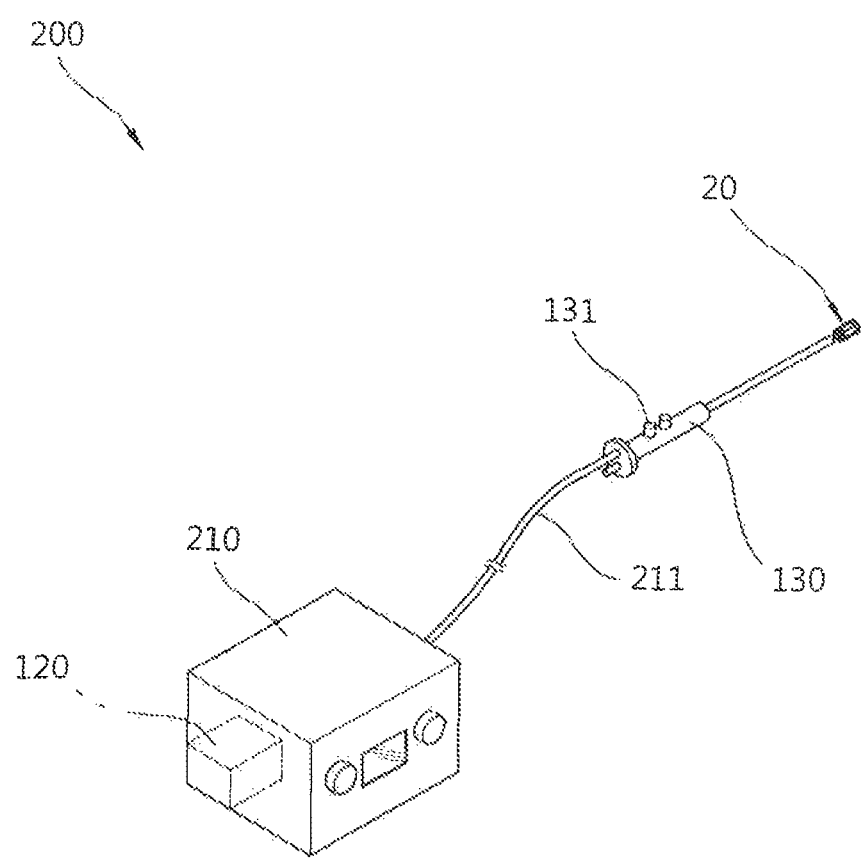
FIG. 6 is a diagram schematically illustrating a configuration of a radiofrequency surgery device according to a second exemplary embodiment.

FIG. 5 is a diagram illustrating an electrode for radiofrequency surgery according to a second exemplary embodiment, and FIG. 6 is a diagram schematically illustrating a configuration of a radiofrequency surgery device according to the second exemplary embodiment.

Referring to FIGS. 5 and 6, some of a plurality of wires 23 may be constituted by positive wires 23a, and the rest of the plurality of wires 23 may be constituted by negative wires 23b. In this case, a first support ring 21a and a second support ring 21b are made of non-conductive materials so as to block the positive wires 23a and the negative wires 23b from being electrically connected to each other.

In addition, a radiofrequency generator 210 is connected to an electrode 20 for radiofrequency surgery by a single cable 211. A positive power supply line connected to the positive wires 23a and a negative power supply line connected to the negative wires 23b may be embedded inside the signal cable 211. In this case, the positive power supply line and the negative power supply line are protected by covering to be electrically shielded from each other. The positive power supply line is connected to the positive wires 23a through the first support ring 21a, and the negative power supply line is connected to the negative wires 23b through the first support ring 21a.

As such, in the electrode 20 electrode for radiofrequency surgery and the radiofrequency surgery device 200 according to the second exemplary embodiment, two electrodes are inserted into the body together, and the shapes thereof are deformed according to the volume of the balloon 12 to generate heat inside the body.

Since the method of controlling the radiofrequency surgery device 200 according to the exemplary embodiment is similar to the method of controlling the radiofrequency surgery device 100 according to the first exemplary embodiment when the process of contacting the opposing electrode 15 with the outer skin of the patient is omitted in the method of controlling the radiofrequency surgery device 100 according to the first exemplary embodiment described above, the method of controlling the radiofrequency surgery device 200 according to the exemplary embodiment may be understood with reference to the method of controlling the radiofrequency surgery device 100 according to the first exemplary embodiment described above.

Third Exemplary Embodiment

Figure 7:
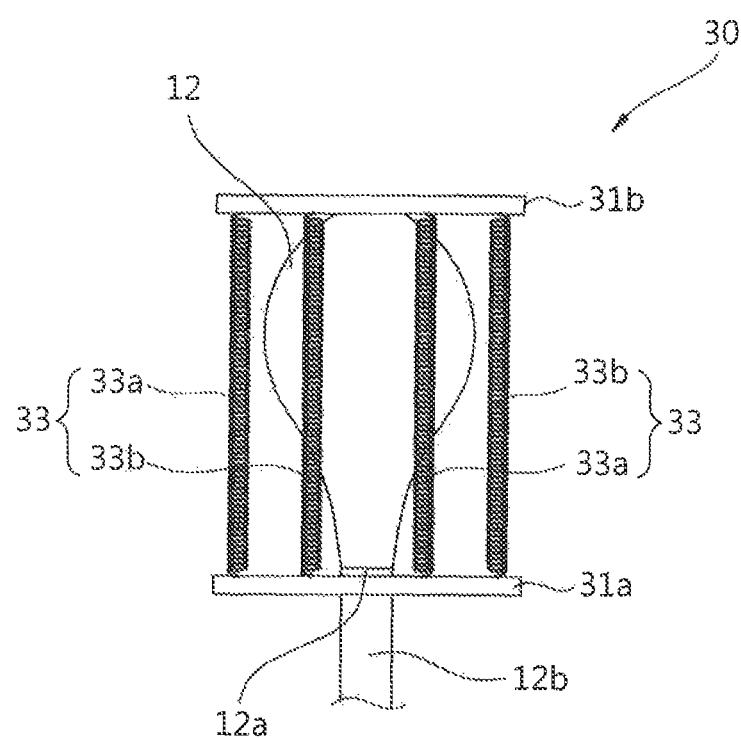
FIG. 7 is a diagram illustrating an electrode for radiofrequency surgery according to a third exemplary embodiment.

FIG. 7 is a diagram illustrating an electrode for radiofrequency surgery according to a third exemplary embodiment.

Referring to FIG. 7, in an electrode 30 for radiofrequency surgery according to a third exemplary embodiment, a plurality of elastic members 33 may be used as a conductor. As an example, the elastic member in the embodiment may be a coil spring.

One end of the plurality of coil springs 33 is coupled with a first support ring 31a, and the other end thereof may be coupled with a second support ring 31b. The plurality of coil springs 33 is arranged to cover the outside of the balloon 12. Accordingly, the shape of the plurality of coil springs 33 may be deformed according to the volume of the balloon 12. That is, the plurality of coil springs 33 maintains a linear shape connecting the first support ring 31a and the second support ring 31b, and may be deformed in an outwardly convex shape while the volume of the balloon 12 is expanded.

In this case, the plurality of coil springs 33 may be implemented to have the same polarity, and the plurality of coil springs 33 may be modified so that some of the plurality of coil springs 33 are constituted by positive coil springs 33a and the rest of the plurality of coil springs 33 are constituted by negative coil springs 33b.

As such, the electrode 30 for radiofrequency surgery according to the third exemplary embodiment may be used in the radiofrequency surgery device 100 according to the first exemplary embodiment or the radiofrequency surgery device 200 according to the second exemplary embodiment described above. Further, a method of controlling a radiofrequency surgery device in which the electrode 30 for radiofrequency surgery according to the third exemplary embodiment is used may be understood with reference to the method of controlling the radiofrequency surgery device 100 according to the first exemplary embodiment.

Fourth Exemplary Embodiment

Figure 8:
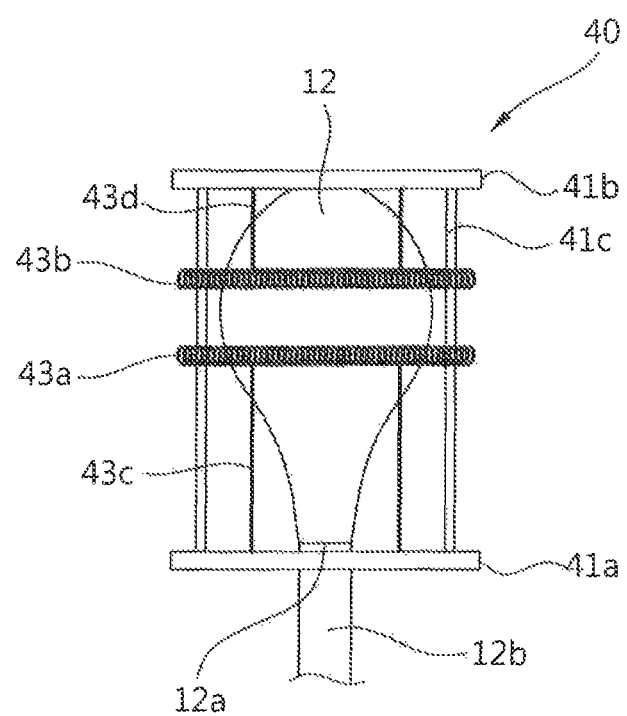
FIG. 8 is a diagram illustrating an electrode for radiofrequency surgery according to a fourth exemplary embodiment.

FIG. 8 is a diagram illustrating an electrode for radiofrequency surgery according to a fourth exemplary embodiment.

Referring to FIG. 8, in an electrode 40 for radiofrequency surgery according to a fourth exemplary embodiment, a first coil spring 43a and a second coil spring 43b having ring shapes covering a circumference of the balloon 12 may be used as a conductor. In this case, a first support ring 41a and a second support ring 41b are connected by a support wire 41c. Further, a first coil wire 43c supporting the first coil spring 43a is coupled with the first support ring 41a, and a second coil wire 43d supporting the second coil spring 43b is coupled with the second support ring 41b.

As an example, when the first coil spring 43a and the second coil spring 43b have the same polarity, the first support ring 41a, the second support ring 41b, the support wire 41c, the first coil wire 43c, and the second coil wire 43d may be constituted by conductors.

As another example, when the first coil spring 43a and the second coil spring 43b have different polarities, the support wire 41c may be made of a non-conductive material. In this case, the first support ring 41a may be connected to a positive power supply line connected to the radiofrequency generator, and the second support ring 41b may be connected to a negative power supply line connected to the radiofrequency generator.

In the electrode 40 for radiofrequency surgery according to the fourth exemplary embodiment, the shapes of the first and second coil springs 43a and 43b may be deformed according to the volume of the balloon 12. That is, the first and second coil springs 43a and 43b usually maintain the ring shapes covering the circumference of the balloon 12, and may be formed in a shape in which an outer diameter of the ring is expanded as the volume of the balloon 12 is expanded.

As such, the electrode 40 for radiofrequency surgery according to the fourth exemplary embodiment may be used in the radiofrequency surgery device 100 according to the first exemplary embodiment or the radiofrequency surgery device 200 according to the second exemplary embodiment described above. Further, a method of controlling a radiofrequency surgery device in which the electrode 40 for radiofrequency surgery according to the fourth exemplary embodiment is used may be understood with reference to the method of controlling the radiofrequency surgery device 100 according to the first exemplary embodiment.

As described above, when the radiofrequency surgery device according to the present invention configured so that the conductor is convexly deformed according to the expansion of the balloon and the radiofrequency current is conducted is particularly used in a lumen of the body, the radiofrequency current may be conducted in the entire cross-sectional area of a corresponding organ, and as a result, the radiofrequency current may be efficiently used.

It should not be appreciated that the exemplary embodiments of the present invention described above and illustrated in the drawings limit the technical spirit of the present invention. The protection scope of the present invention is limited by only matters described in the claims and the technical spirit of the present invention can be modified and changed in various forms by those skilled in the art. Accordingly, the modification and the change will belong to the protection scope of the present invention as long as the modification and change are apparent to those skilled in the art.

The invention claimed is:

1. An electrode for radiofrequency surgery, comprising:
   a balloon having a volume with an inside portion and an outside portion;
   a conductor which is arranged at the outside portion of the balloon and has an exterior shape which varies according to the volume of the balloon;
   first and second support rings which are spaced apart from each other with the balloon therebetween, wherein the conductor is a plurality of elastic members, which are provided in a ring shape covering a circumference of the balloon and arranged between the first support ring and the second support ring;
   a first wire connecting some of the plurality of elastic members and the first support ring; and
   a second wire connecting the second support ring and the plurality of elastic members which are not connected to the first support ring among the plurality of elastic members;
   wherein the first wire is not directly physically connected to the second support ring and the second wire is not directly physically connected to the first support ring.

2. The electrode of claim 1, wherein the balloon is supported by at least one of the first or the second support ring.

3. The electrode of claim 1, further comprising:
   a support wire connecting the first support ring and the second support ring.

4. The electrode of claim 1, wherein the plurality of elastic members are arranged parallel to the first support ring and the second support ring.

5. The electrode of claim 1, wherein the first support ring and the second support ring are composed of a conductive material.

6. The electrode for radiofrequency surgery of claim 1, wherein the first wire and the second wire are composed of conductive material.

7. A radiofrequency surgery device, comprising:
a balloon having a volume with an inside portion and an outside portion;
a pump connected to the balloon to supply gas to the balloon;
a conductor arranged on the outside portion of the balloon and having an exterior shape which varies according to the volume of the balloon;
a radiofrequency generator electrically connected to the conductor to generate a radiofrequency current;
first and second support rings which are spaced apart from each other with the balloon therebetween, wherein the conductor is a plurality of elastic members which are provided in parallel to the first support ring and the second support ring and arranged between the first support ring and the second support ring;
a first wire connecting some of the plurality of elastic members and the first support ring; and
a second wire connecting the second support ring and the plurality of elastic members which are not connected to the first support ring among the plurality of elastic,
wherein the first wire is not directly physically connected to the second support ring and the second wire is not directly physically connected to the first support ring.

8. The device of claim 7, wherein the balloon is supported by at least one of the first or the second support ring.

9. The device of claim 7, wherein the plurality of elastic members are provided in a ring shape covering a circumference of the balloon.

10. A method of controlling a radiofrequency surgery device, comprising:
inserting an electrode into a body;
injecting gas into a balloon provided in the electrode to expand the balloon, whereby expanding an exterior shape of the electrode; and
supplying a radiofrequency current to the electrode,
wherein the electrode comprises:
a conductor which is arranged at an outside portion of the balloon and has a shape which varies according to a volume of the balloon;
first and second support rings which are spaced apart from each other with the balloon therebetween, wherein the conductor is a plurality of elastic members, which are provided in a ring shape covering a circumference of the balloon and arranged between the first support ring and the second support ring;
a first wire connecting some of the plurality of elastic members and the first support ring; and
a second wire connecting the second support ring and the plurality of elastic members which are not connected to the first support ring among the plurality of elastic members;
wherein the first wire is not directly physically connected to the second support ring and the second wire is not directly physically connected to the first support ring.

11. The method of claim 10, further comprising:
applying one of a positive current or a negative current to the electrode;
contacting a return electrode to an outer skin; and
applying a current which is opposite to the electrode to the return electrode.

12. The method of claim 10, further comprising applying a positive current and a negative current to the electrode, wherein the electrode is divided into a positive pole and a negative pole, wherein the positive current is applied to the positive pole and the negative current is applied to the negative pole.

* * * * *